United States Patent
Kim et al.

(10) Patent No.: US 10,682,384 B2
(45) Date of Patent: Jun. 16, 2020

(54) COMPOSITION COMPRISING NATURAL COMPLEX EXTRACT AS ACTIVE INGREDIENT

(71) Applicants: COSMAX NS, INC., Seoul (KR); COSMAX NBT, INC., Seoul (KR)

(72) Inventors: Jin Hak Kim, Seoul (KR); Kwang Soo Baek, Seoul (KR); Yong Jun Jo, Seoul (KR); Hyeon Yeong Ahn, Seoul (KR); Young Min Park, Gyeonggi-do (KR); Hyun Ji Kim, Gyeonggi-do (KR); Jae Seok Shim, Gyeonggi-do (KR); Su Young Choi, Seoul (KR); Jin Woo Lee, Seoul (KR); Sang Woo Kim, Gyeonggi-do (KR); Mann-Seok Yoon, Gyeonggi-do (KR); Jin Hyouk Kwon, Seoul (KR)

(73) Assignees: COSMAX NS, INC., Seoul (KR); COSMAX NBT, INC., Seoul (KR)

( * ) Notice: Subject to any disclaimer, the term of this patent is extended or adjusted under 35 U.S.C. 154(b) by 0 days.

(21) Appl. No.: 15/866,673

(22) Filed: Jan. 10, 2018

(65) Prior Publication Data
US 2018/0243361 A1 Aug. 30, 2018

Related U.S. Application Data

(60) Provisional application No. 62/464,605, filed on Feb. 28, 2017.

(51) Int. Cl.
*A61K 36/60* (2006.01)
*A61Q 19/02* (2006.01)
(Continued)

(52) U.S. Cl.
CPC .......... *A61K 36/815* (2013.01); *A61K 8/9789* (2017.08); *A61K 36/44* (2013.01);
(Continued)

(58) Field of Classification Search
CPC ........ A61K 2236/331; A61K 2800/805; A61K 36/44; A61K 36/532; A61K 36/60;
(Continued)

(56) References Cited

U.S. PATENT DOCUMENTS

2006/0018867 A1* 1/2006 Kawasaki .............. A61K 8/898
424/70.122
2006/0198810 A1 9/2006 Murray et al.

FOREIGN PATENT DOCUMENTS

| JP | 1997-071527 A | 3/1997 |
| KR | 10-1999-0081362 A | 11/1999 |
| KR | 10-2009-0047916 A | 5/2009 |
| KR | 10-2012-0077357 A | 7/2012 |
| KR | 10-2014-0133739 A | 11/2014 |

OTHER PUBLICATIONS

Tawfik et al. (Journal of Food and Nutrition Sciences 2014; 2(4): 138-145). (Year: 2014).*

(Continued)

*Primary Examiner* — Ernst V Arnold
(74) *Attorney, Agent, or Firm* — Christensen, Fonder, Dardi; Diane E. Bennett; Peter S. Dardi

(57) ABSTRACT

The present invention relates to a composition comprising a natural complex extract. It is confirmed that the composition has synergistic effects on antioxidant activity, immune enhancement, whitening, anti-wrinkle and collagenase inhibition with low cytotoxicity, and therefore, the composition is suitable for uses of antioxidation, immune, whitening and skin anti-wrinkle.

4 Claims, 4 Drawing Sheets

(51) Int. Cl.
| | | |
|---|---|---|
| *A61K 36/815* | (2006.01) | |
| *A61K 36/532* | (2006.01) | |
| *A61K 8/9789* | (2017.01) | |
| *A61Q 19/08* | (2006.01) | |
| *A61K 36/44* | (2006.01) | |
| *A61K 36/534* | (2006.01) | |

(52) U.S. Cl.
CPC .......... *A61K 36/532* (2013.01); *A61K 36/534* (2013.01); *A61K 36/60* (2013.01); *A61Q 19/02* (2013.01); *A61Q 19/08* (2013.01); *A61K 2236/331* (2013.01); *A61K 2800/5922* (2013.01); *A61K 2800/805* (2013.01)

(58) Field of Classification Search
CPC .... A61K 36/815; A61K 8/9789; A61Q 19/02; A61Q 19/08
See application file for complete search history.

(56) References Cited

OTHER PUBLICATIONS

English translation of CN1170583 1998 3 pages. (Year: 1998).*
Solomon et al. (J Agric Food Chem. 2006;54:7717-7723) (Year: 2006).*
Sakanaka et al. (Food Chemistry 2005;89:569-575) (Year: 2005).*
Park et al. (Antioxidants 2019;8(75):12 pages) (Year: 2019).*
Cheng et al. (Drug Design, Development and Therapy 2015; 33-78) (Year: 2015).*
Marketwatch Press release May 3, 2017 from https://www.marketwatch.com/press-release/ nerium-international-embarks-on-inside-out-approach-to-overall-wellness-with-introduction-of-youth-factortm-complete-vitality-complex-and-superfood-antioxidant-boost-2017-05-03; 4 pages. (Year: 2019).*
Office Action for corresponding Korean Application No. 10-2017-0027152 dated Feb. 10, 2020. (Google translation).

* cited by examiner

COMPOSITION COMPRISING NATURAL COMPLEX EXTRACT AS ACTIVE INGREDIENT

CROSS REFERENCE TO RELATED APPLICATIONS

This application claims priority to U.S. provisional patent application 62/464,605 to Kim et al., entitled "Compositions Comprising Heat Water Extract of Gojiberry, Fig, and Agastache Rugosa as Active Ingredients," incorporated herein by reference.

TECHNICAL FIELD

The present invention relates to a composition for antioxidation, immune enhancement and skin-ageing prevention comprising a natural complex extract as an active ingredient.

BACKGROUND ART

Due to the recent development of science technology and modern medicine, the average life expectancy of humans is gradually increasing, and therefore, interest for health is increasing to improve the quality of life. This trend is increasing regardless of generation and age. Further, as interests in medicines, health supplements, and cosmetics, which include natural products, has increased, research and development are increasing. In particular, the efficacy of natural medicines and the function of health supplements and cosmetics including natural products are expanding to basic medical areas such as antioxidation, cholesterol suppression, obesity prevention effect, immunity, disease prevention and aging suppression.

Goji berry is also known as Chinese boxthorn or Matrimony vine, and has various species belonging to the Solanacea family, *Lycium* genus. Among the various species belonging to the *Lycium* genus, *Lycium barbarum* and *Lycium chinense* are most commonly used in oriental medicine. For example, *Lycium barbarum* fruit also known as *Fructus lycii* has long been known as a medicinal plant that helps maintain health in, particularly, Asia in general. Further, recent studies report that the *Lycium barbarum* not only enhances and regulates the immune system but also has properties of anti-aging, anticancer, reduced blood levels of fat and sugar, and reduced arterial blood pressure. U.S. Patent Publication No. 2006/0198810 discloses the efficacy of, in particular, a mixture of an extract of rose fruits and *Angelica dahurica* (Chinese angelica) and an extract of wolfberry, which promotes lipogenesis of skin cells. Further, characteristics of specific components of the *Lycium barbarum* are already known. According to this, zeaxanthin dipalmitate is known to have antioxidant and anti-inflammatory characteristics, but *Lycium barbarum* polysaccharide (LBP) and 2-O-(β-D-glucopyranosyl)-ascorbic acid (vitamin C derivative) are known to have immune stimulatory and antioxidant characteristics.

Fig tree (*Ficus carica* L) is deciduous shrub belonging to Moraceae family and is native to the Mediterranean cost of Wester Asia. It grows to a height of 2 m to 4 m, its bark is light gray, and its leaf comes alternatively, is thick and wide egg-shaped, and has rough surface and hairs on its back. It is known that its latex has effects on athlete's foot, boil, hemorrhoids, its leaf has effects on athlete's foot or neuralgia, its fruit has effects on lowering blood pressure, constipation and the like. Korean Patent Registration No. 10-0512285 discloses a soap composition for medical use comprising an extract of fig fruit or leaf, which has antifungal and antibacterial effects.

Korean mint (*Agastache rugosa* (Fisch. et Meyer) O. Kuntze, betony) is a perennial herb belonging to the Labiatae family and its dried aboveground part and whole plant are used as a medicine. Its scientific name is *Teucrium chamaedrys* or *Agastache rugosa* (Latin name: *Agastachis herba*), and in China, *Pogostemon cablin* (Latin name: *Pogostemonis herba*) belonging to the same family is used mixedly with the *Agastache rugosa*. Korean mint has been traditionally used as an oriental medicine for anorexia, vomit, strong stomach, diarrhea, antipyretic action and the like (Ben Cao Gang Mu (Compendium of Materia Medica)), and there are studies about an external skin preparation for moisturizing and lubricating a keratin layer which comprises amino acids and plant extracts of Korean mint and the like (Japanese Patent Laid-Open Publication No.9-71527) and the like. Through studies for components of Korean mint, materials such as methyl chavicol, rosmarinic acid, anethole and the like are reported.

Persimmon leaf contains vitamin C, chlorophyll, polyphenol and the like, and it is reported that it has effects on stopping internal hemorrhage, stopping bleeding caused by an ulcer in the digestive tract, and deodorization. Further, it is known that it is helpful when the throat is swollen and voice is cracked, and also has antihypertensive action like the acerb component of the persimmon.

The present inventors have studied for a material originated from nature for antioxidation, immune enhancement, whitening, skin anti-ageing, and as a result, have found that a composition comprising a complex extract of goji berry, fig and Korean mint, or goji berry, fig and persimmon leaf shows not only the synergistic effect on antioxidation, immune enhancement, whitening, anti-wrinkle and collagenase inhibition activities but also low cytotoxicity, thereby completing the present invention.

DISCLOSURE

Technical Problem

One object of the present invention is to provide a composition for antioxidation, immune enhancement, whitening, collagenase inhibition, collagen production stimulation and anti-wrinkle, which comprises a natural complex extract as an active ingredient.

Technical Solution

The present invention provides a composition for antioxidation comprising a natural complex extract as an active ingredient.

In one aspect, the present invention provides a composition for antioxidation comprising an extract of goji berry, fig and Korean mint as an active ingredient.

In another aspect, the present invention provides a composition for immune enhancement comprising an extract of goji berry, fig and Korean mint as an active ingredient. The term "immune enhancement" used herein means increasing the immune response or activity of the in vivo immune system.

In further aspect, the present invention provides a composition for skin whitening comprising an extract of goji berry, fig and Korean mint as an active ingredient. The term "skin whitening" used herein means the result of inhibition of melanin production, and specifically, it can be understood as an improvement in symptoms caused by increased melanin such as stains, freckles, skin-aging and the like, as the melanin production is inhibited.

In further another aspect, the present invention provides a composition for collagenase inhibition comprising an extract of goji berry, fig and Korean mint as an active ingredient.

In still another aspect, the present invention provides a composition for anti-wrinkle comprising an extract of goji berry, fig and Korean mint as an active ingredient.

In still another aspect, the present invention provides a composition for antioxidation comprising an extract of goji berry, fig and persimmon leaf as an active ingredient.

In still another aspect, the present invention provides a composition for immune enhancement comprising an extract of goji berry, fig and persimmon leaf as an active ingredient.

In still another aspect, the present invention provides a composition for skin whitening comprising an extract of goji berry, fig and persimmon leaf as an active ingredient.

In still another aspect, the present invention provides a composition for collagenase inhibition comprising an extract of goji berry, fig and persimmon leaf as an active ingredient.

In still another aspect, the present invention provides a composition for anti-wrinkle comprising an extract of goji berry, fig and persimmon leaf as an active ingredient.

When the extract is obtained by treating an extraction solvent, various extraction solvent may be used, and preferably, it may be a polar solvent. The suitable polar solvent may be purified water, alcohols (methanol, ethanol, propanol, butanol, normal-propanol, iso-propanol, normal-butanol, 1-pentanol, 2-butoxyethanol or ethylene glycol and the like), acetic acid, dimethyl-formamide (DMF) and dimethyl sulfoxide (DMSO), and more preferably, the extraction solvent which can be used in the present invention may be purified water, $C_{1-4}$ anhydrous or hydrous low alcohols (methanol, ethanol, propanol, butanol and the like) and a mixture solvent of the low alcohol and the purified water. Most preferably, the extract of the present invention may be a hot water extract.

The term "extract" used herein has the meaning that is commonly known as a crude extract in the art as described above, but also includes fractions obtained by additionally fractionating the extract in a broad sense. Namely, the extract according to the present invention is obtained by using the extraction solvent described above, and also obtained by further applying a purification process. For example, the fractions obtained through a ultrafiltration membrane having a certain molecular cut-off value from the extract, and fractions obtained through various purification methods further performed, such as an isolation by using various chromatographs (manufactured for isolating according to size, charge, hydrophobic or affinity) are also included as the extract. Further, the extract according to the present invention may be prepared in a type of powder through a further process, such as re-extraction, vacuum distillation, freeze-drying, spray drying or a combination thereof.

According to one embodiment of the present invention, the extract may be extracted after mixing (i) 5-20 parts by weight, or 7-12 parts by weight, or 10-15 parts by weight of goji berry; (ii) 5-20 parts by weight, or 7-12 parts by weight, or 10-15 parts by weight of fig; and (iii) 60-90 parts by weight, or 65-85 parts by weight, or 70-80 parts by weight of Korean mint.

According to another embodiment, the extract may be extracted after mixing (i) 5-20 parts by weight, or 7-12 parts by weight, or 10-15 parts by weight of goji berry; (ii) 5-20 parts by weight, or 7-12 parts by weight, or 10-15 parts by weight of fig; and (iii) 60-90 parts by weight, or 65-85 parts by weight, or 70-80 parts by weight of persimmon leaf.

According to one embodiment of the present invention, the extract may be manufactured by mixing each extract of goji berry, fig and Korean mint at a weight ratio of 1:1:1, 2:1:1 or 2:1:2.

According to another embodiment, the extract may be manufactured by mixing each extract of goji berry, fig and persimmon leaf at a weight ratio of 1:1:1, 2:1:1 or 2:1:2.

According to one embodiment of the present invention, the composition of the present invention is a pharmaceutical composition comprising a pharmaceutically effective amount of the extract of goji berry, fig and Korean mint of the present invention; and a pharmaceutically acceptable carrier.

According to another embodiment, the composition of the present invention is a pharmaceutical composition comprising a pharmaceutically effective amount of the extract of goji berry, fig and persimmon leaf of the present invention; and a pharmaceutically acceptable carrier.

The term "pharmaceutically effective amount" used herein means an amount sufficient to attain efficacy or activity of the extract described above.

When the composition of the present invention is manufactured into a pharmaceutical composition, the pharmaceutical composition of the present invention contains a pharmaceutically acceptable carrier. The pharmaceutically acceptable carrier contained in the pharmaceutical composition of the present invention is ordinarily used at the time of formulation, and it may include, but not limited to, lactose, dextrose, sucrose, sorbitol, mannitol, starch, acacia gum, calcium phosphate, alginate, gelatin, calcium silicate, microcrystalline cellulose, polyvinyl pyrrolidone, cellulose, water, syrup, methyl cellulose, methyl hydroxy benzoate, propyl hydroxy benzoate, talc, magnesium stearate and mineral oil. The pharmaceutical composition of the present invention may further contain, in addition to the above ingredients, a lubricant, a wetting agent, a sweetening agent, a flavoring agent, an emulsifier, a suspending agent, a preservative and the like. Further, the pharmaceutical composition of the present invention may be administered orally or parenterally, and preferably parenterally.

A suitable dose of the pharmaceutical composition of the present invention may vary depending on various factors, such as the method for formulation, the manner of administration, the age, body weight, gender and morbidity of the patient, the diet, the time of administration, the route of administration, the excretion rate, and response sensitivity. Meanwhile, a general dose of the pharmaceutical composition of the present invention is within the range of 0.0001 mg/kg to 1000 mg/kg.

Another aspect of the present invention provides a food composition comprising an extract of goji berry, fig and Korean mint as an active ingredient.

Further aspect of the present invention provides a food composition comprising an extract of goji berry, fig and persimmon leaf as an active ingredient.

The food composition according to the present invention includes all types of a functional food, a nutritional supplement, a health food, a food additives and the like. The types may be manufactured to various types by the conventional methods known in the art. For example, for the health food, the natural plant extract according to the present invention may be prepared in the form of tea, juice and drink, or it may be granulized, encapsulated or powdered. Further, the extract of the present invention may be mixed with a substance or active ingredient known to have an effect of immune enhancement, whitening, collagenase inhibition, collagen production stimulation and anti-wrinkle to prepare a composition.

When the composition of the present invention is manufactured into a food composition, the food composition contains ingredients that are commonly added at the time of food manufacturing, for example, proteins, carbohydrates, fats, nutrients, seasoning, and flavoring agents, in addition to the extract of goji berry, fig and Korean mint and the extract of goji berry, fig and persimmon leaf as an active ingredient. Examples of the carbohydrate described above may include normal sugars (monosaccharides, such as glucose and fructose; disaccharides, such as maltose, sucrose and oligosaccharides; and polysaccharides, such as dextrin and cyclodextrin) and sugar alcohols, such as xylitol, sorbitol and erythritol. Examples of the flavoring agent may include natural flavoring agents (thaumatin, and stevia extract (e.g., rebaudioside A, glycyrrhizin, etc.)) and synthetic flavoring agents (saccharin, aspartame, etc.). For example, when the food composition of the present invention is manufactured into a drink, the composition may further contain, in addition to the extract of the present invention, citric acid, liquefied fructose, sugar, glucose, acetic acid, malic acid, fruit juice, *Eucommia ulmoides* extract, jujube extract, licorice extract and the like.

The preferable content of the natural complex extract of the present invention in the composition of the present invention may be 0.01 wt % to 100 wt % or 0.01 wt % to 50 wt % in the final product. The natural plant extract of the present invention may be manufactured into powder or concentrate to be used as food additives.

Further another aspect of the present invention provides a cosmetic composition comprising the natural complex extract of the present invention as an active ingredient.

The cosmetic composition according to the present invention may be manufactured into various forms, and in this case, the composition may be manufactured by containing a carrier and the like commonly used in the formulations of the cosmetic composition. According to one embodiment, the carrier may be contained in an amount of about 1 wt % to about 99.99 wt %, preferably about 5 wt % to about 99 wt % based on the total weight of the cosmetic composition of the present invention.

According to one embodiment, the cosmetic composition may be formulated in the form of solutions, suspensions, emulsions, pastes, gels, creams, lotions, powders, soaps, surfactant-containing cleansings, oils, powder foundation, emulsion foundation, wax foundation and spray foundation, but not limited thereto. More specifically, when the composition of the present invention is used as a cosmetic composition, the composition may be manufactured into a formulation selected from the group consisting of a basic cosmetic formulation selected from toners, emulsions, creams, essences, gels, packs and cleansing creams; and a make-up cosmetic formulation such as foundations.

When the cosmetic composition according to one embodiment is formulated in the form of pastes, creams or gels, animal oils, vegetable oils, wax, paraffin, starch, tragacanth, cellulose derivatives, polyethylene glycol, silicon, bentonite, silica, talc, zinc oxide and the like may be used as a carrier component. When the composition of the present invention is formulated in the form of powders or sprays, lactose, talc, silica, aluminum hydroxide, calcium silicate or polyamide powder may be used as a carrier component, and in particular, in the form of sprays, a propellant, such as chlorofluorohydrocarbon, propane/butane or dimethyl ether may be additionally contained.

When the cosmetic composition according to one embodiment is formulated in the form of solutions or emulsions, a solvent, a solubilizer or an emulsifier may be used as a carrier component. For example, water, ethanol, isopropanol, ethyl carbonate, ethyl acetate, benzyl alcohol, benzyl benzoate, propylene glycol, 1,3-butyl glycol oil, glycerol aliphatic esters, polyethylene glycol or fatty acid sorbitan esters may be used.

When the cosmetic composition according to one embodiment is formulated in the form of suspensions, liquid diluents such as water, ethanol or propylene glycol; suspensions such as ethoxylated isostearyl alcohol, polyoxyethylene sorbitol esters and polyoxyethylene sorbitan esters; microcrystalline cellulose, aluminum metahydroxide, bentonite, agar or tragacanth may be used as a carrier component.

Advantageous Effects

The composition of the present invention comprising a natural complex extract as an active ingredient has excellent effects on antioxidation, immune enhancement, whitening, collagenase inhibition, collagen production stimulation and anti-wrinkle by synergistic action.

BEST MODE FOR CARRYING OUT THE INVENTION

Figure 1:
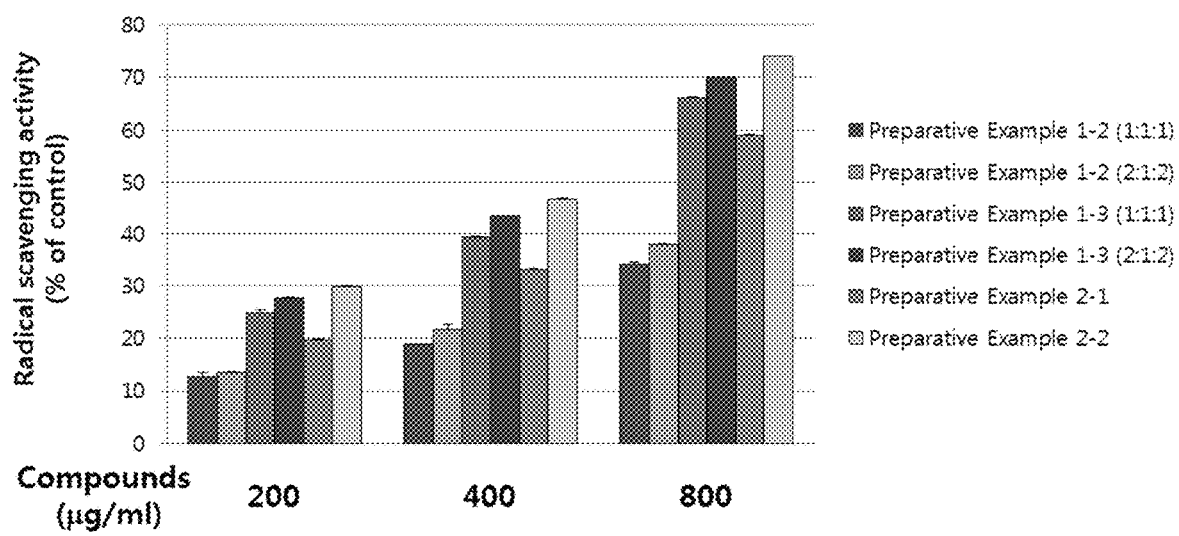
FIG. 1 is a graph showing the antioxidative effect of the natural complex extract.

Various changes in form and details may be made to the presently disclosed embodiment and thus should not be construed as being limited to the aspects set forth herein. The presently disclosed embodiment is not limited to the aspects described in the present description, and thus it should be understood that the presently disclosed embodiment does not include every kind of variation example or alternative equivalent included in the spirit and scope of the presently disclosed embodiment. Also, while describing the aspects, detailed descriptions about related well-known functions or configurations that may diminish the clarity of the points of the aspects of the presently disclosed embodiment will be omitted.

PREPARATIVE EXAMPLE 1

Preparative Example 1-1

Each of goji berry 50 g, fig 50 g, Korean mint 50 g and persimmon leaf 50 g was mixed with 10 times of distilled water, and then heated and extracted at 95° C. for 4 hours by using a heating mantle equipped with a reflux cooling system. The extract was filtered through a filter paper (Whatman No. 2), concentrated at reduced pressure and at a temperature of 50° C. to 60° C., pre-frozen at a temperature of −40° C., and then dried at −40° C. for 48 hours by using a freeze dryer to the water content of 3% to 5%, to obtain each extract.

Preparative Example 1-2

The goji berry extract, the fig extract and Korean mint extract of Preparative Example 1-1 were mixed at weight ratio of 1:1:1 and 2:1:2, respectively.

Preparative Example 1-3

The goji berry extract, the fig extract and the persimmon leaf extract of Preparative Example 1-1 were mixed at weight ratio of 1:1:1 and 2:1:2, respectively.

PREPARATIVE EXAMPLE 2

Preparative Example 2-1

Goji berry 14.93 g, fig 9.29 g and Korean mint 75.78 g were mixed, 10 times of distilled water was added thereto, and then heated and extracted at 95° C. for 4 hours by using a heating mantle equipped with a reflux cooling system. The extract was filtered, concentrated and then spray dried to obtain an extract.

Preparative Example 2-2

Goji berry 17.5 g, fig 10.8 g and persimmon leaf 71.7 g were mixed, 10 times of distilled water was added thereto, and then heated and extracted at 95° C. for 4 hours by using a heating mantle equipped with a reflux cooling system. The extract was filtered, concentrated and then spray dried to obtain an extract.

TEST EXAMPLE 1

Measurement of Antioxidant Activity

Antioxidative effect was examined by using 2,2-diphenyl-1-picrylhydrazyl (DPPH). Each sample was added to the DPPH (250 μM) solution (Positive control: Vitamin C, 50 μg/mL), and a reaction was induced at 37° C. for 30 min. The antioxidation effect was calculated from OD values obtained by measuring absorbance at 517 nm after the reaction was completed, and the results were shown in FIG. 1.

As shown in FIG. 1, from the results of measuring the antioxidative effect at the test group wherein each of the goji berry, the fig and Korean mint was extracted with hot water and then they were mixed at the ratios of 1:1:1 and 2:1:2, respectively; and the test group wherein the goji berry, the fig and Korean mint of 14.93, 9.29 and 75.78 parts by weight, respectively, were mixed, and then extracted and spray-dried, it was confirmed that the antioxidative effect of the test group of extracting after mixing showed the highest antioxidative effect. From the results of measuring the antioxidative effect at the test group wherein each of the goji berry, the fig and the persimmon leaf was extracted with hot water and then they were mixed at the ratios of 1:1:1 and 2:1:2, respectively; and the test group wherein the goji berry, the fig and the persimmon leaf of 17.5, 10.8 and 71.7 parts by weight, respectively, were mixed, and then extracted and spray-dried, it was confirmed that the antioxidative effect of the test group of extracting after mixing showed the highest antioxidative effect. From FIG. 1, it was confirmed that the method of mixing the goji berry, the fig and Korean mint and then extracting the mixture showed more remarkable synergistic effect on the antioxidative efficacy than the method of extracting each of the goji berry, the fig and Korean mint separately, and then mixing the extracts.

TEST EXAMPLE 2

Measurement of Cell Viability 2-1. Cell Culture

Mouse macrophage cell line, RAW264.7 cells were cultured at the density of 70% to 80% in a 100 mm cell culture dish with RPMI 1640 medium containing penicillin (100 IU/ml), streptomycin (100 μg/ml) and 10% FBS.

2-2. Measurement of Cell Viability

The cell viability was analyzed by using MTT (3-[4,5-dimethylthiazol-2-yl]-2,5-diphinyltetrazolium bromide) assay. The concentration of the cultured mouse macrophage cell line, RAW264.7 was controlled by using RPMI 1640 medium to $1\times10^6$ cell/ml. The cells were inoculated in a 96 well plate, and pre-cultured for 18 hours at a condition of 5% $CO_2$ and 37° C. Then the medium was removed and medium containing the extracts at a concentration of 100, 200 and 400 μg/mL, respectively, was added thereto, and the cells were cultured. After 24 hours, MTT solution (stock concentration: 5 mg/ml) 10 μl was added thereto and an additional reaction was induced for 3 hours. For completing the reaction and dissolving formazan crystal, DMSO 100 μl was additionally added to each well. As the cell viability, the amount that the MTT was reduced to the formazan was calculated from OD values obtained by measuring absorbance at 570 nm, and the results were shown in FIG. 2.

Figure 2:
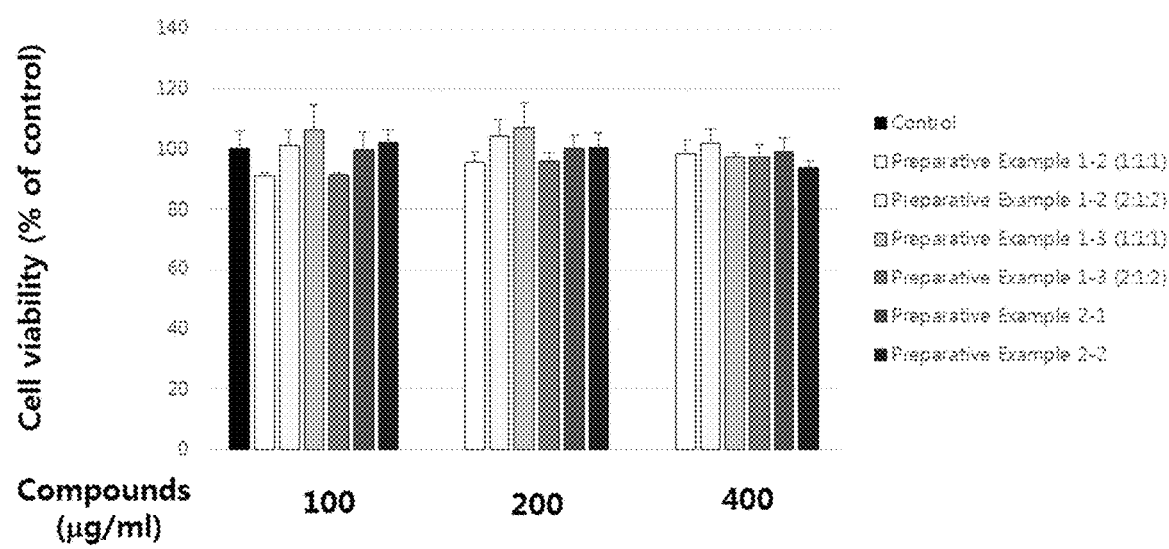
FIG. 2 is a graph showing the cell viability of the natural complex extract.

As shown in FIG. 2, it was confirmed that the cell viabilities of the group wherein each of the goji berry, the fig and Korean mint was separately extracted with hot water and then they were mixed at the ratios of 1:1:1 and 2:1:2, respectively; and the group wherein the goji berry, the fig and Korean mint of 14.93, 9.29 and 75.78 parts by weight, respectively, were mixed, and then extracted and spray-dried are within the range from 80% to 120%. It was confirmed that the cell viabilities of the group wherein each of the goji berry, the fig and the persimmon leaf was extracted with hot water and then they were mixed at the ratios of 1:1:1 and 2:1:2, respectively; and the group wherein the goji berry, the fig and the persimmon leaf of 17.5, 10.8 and 71.7 parts by weight, respectively, were mixed, and then extracted and spray-dried are within the range from 80% to 120%. From the results, it was confirmed that the extracts did not affect to the cell viability at the concentration range tested above.

TEST EXAMPLE 3

Immune Enhancement Effect According to Extract Concentration—Measurement of Macrophage-derived TNF-α Production The concentration of the cultured mouse macrophage cell line, RAW264.7 was controlled by using RPMI 1640 medium to $1\times10^6$ cell/ml. The cells were inoculated in a 96 well plate, and pre-cultured for 18 hours at a condition of 5% $CO_2$ and 37° C. Then the medium was removed and medium containing positive control (LPS, 100 ng/mL) and the extracts at a concentration of 100, 200 and 400 μg/mL, respectively, was added thereto, and the cells were cultured. After 24 hours, the supernatant 100 μl was transferred to another 96 well plate, the TNF-α concentration was measured by using an enzyme-linked immunosorbent assay (ELISA) kit of R&D systems according to instructions of the manufacturer. The results were shown in FIG. 3.

Figure 3:
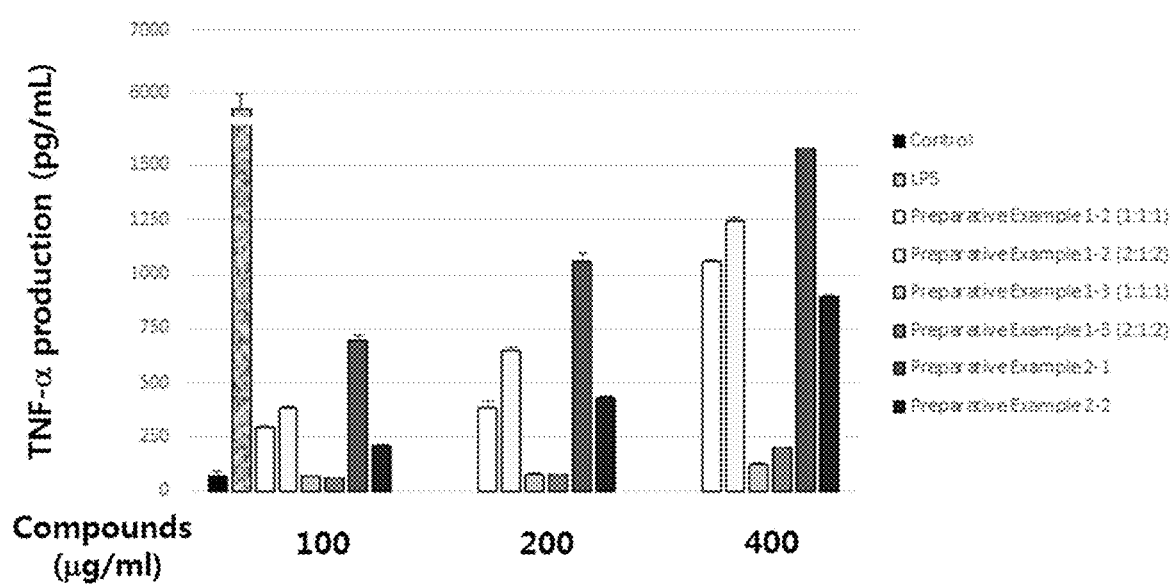
FIG. 3 is a graph showing the effect of the natural complex extract on the TNF-α production rate of macrophages.

As shown in FIG. 3, from the results of measuring the TNF-a production at the test group wherein each of the goji berry, the fig and Korean mint was separately extracted with hot water and then they were mixed at the ratios of 1:1:1 and 2:1:2; and the test group wherein the goji berry, the fig and Korean mint of 14.93, 9.29 and 75.78 parts by weight, respectively, were mixed, and then extracted and spray-dried, it was confirmed that the TNF-α production of the test group of extracting after mixing showed the highest antioxidative effect. From the results of measuring the TNF-α production at the group wherein each of the goji berry, the fig and the persimmon leaf was separately extracted with hot water and then they were mixed at the ratios of 1:1:1 and 2:1:2; and the group wherein the goji berry, the fig and the persimmon leaf of 17.5, 10.8 and 71.7 parts by weight, respectively, were mixed, and then extracted and spray-dried, it was confirmed that the TNF-α production of the test group of extracting after mixing showed the highest antioxidative effect. From the results, it was confirmed that the method of mixing the goji berry, the fig, Korean mint and the persimmon leaf and then extracting the mixture showed more remarkable synergistic effect on the immune enhancement efficacy than the method of extracting each of the goji berry, the fig, Korean mint and the persimmon leaf separately, and then mixing the extracts.

TEST EXAMPLE 4

Measurement of Melanin Production 4-1. Cell Culture

Mouse melanoma cell line, B16-F10 cells were cultured the density of 70% to 80% in a 100 mm cell culture dish with DMEM medium containing penicillin (100 IU/ml), streptomycin (100 μg/ml) and 10% FBS.

4-2. Measurement of Melanin Concentration

The concentration of the cultured mouse melanoma cell line, B16-F10 cell was controlled by using DMEM medium containing penicillin (100 IU/ml), streptomycin (100 μg/ml) and 10% FBS to $1 \times 10^5$ cell/ml. The cells were inoculated in a 12 well plate, and pre-cultured for 18 hours at a condition of 5% $CO_2$ and 37° C. Then the medium was removed, and medium containing the extracts at a concentration of 1000 μg/mL, respectively, and alpha-Melanocyte-stimulating hormone (α-MSH) were added thereto at the same time. The cells were cultured for 24 hours, the medium was removed, and then 1N NaOH was added thereto for dissolving melanin. The melanin content was calculated from OD values obtained by measuring absorbance at 405 nm, and the results were shown in FIG. 4.

Figure 4:
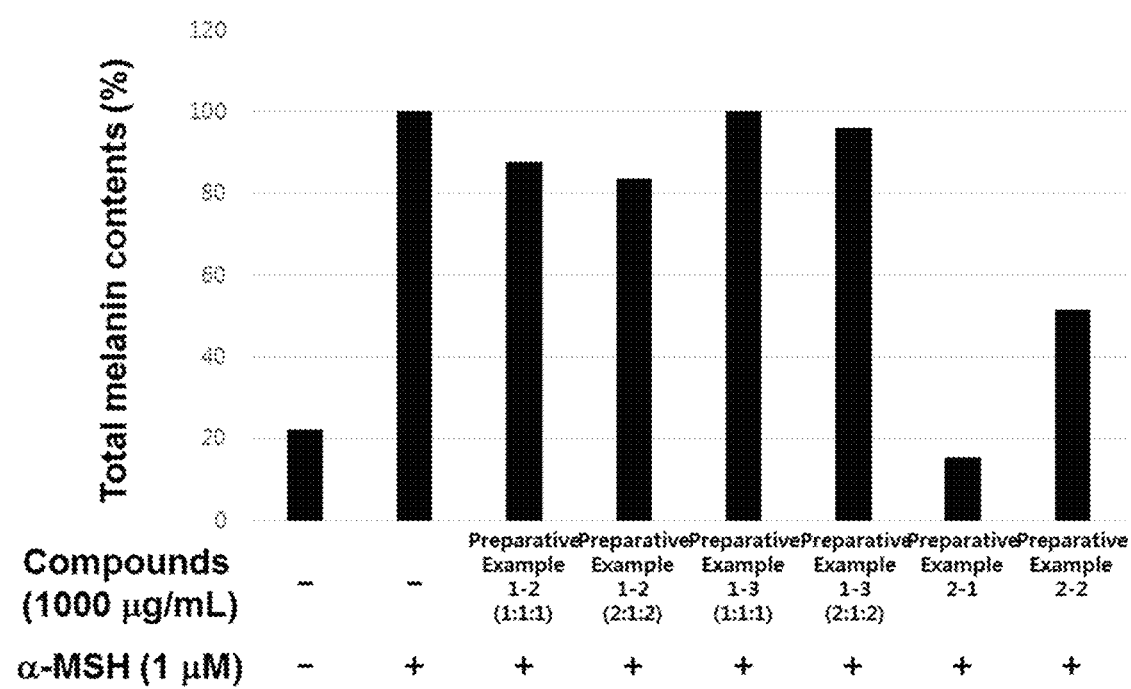
FIG. 4 is a graph showing the effect of the natural complex extract on the melanin production.

As shown in FIG. 4, from the results of measuring the melanin production at the group extracting each of the goji berry, the fig and Korean mint with hot water and mixing the three extracts at a ratio of 1:1:1 and 2:1:2, respectively; and the group mixing the goji berry, the fig and Korean mint of 14.93, 9.29 and 75.78 parts by weight, respectively, and then extracting and spray drying the mixture, it was confirmed that the melanin production was reduced. From the results of measuring the melanin production at the group extracting each of the goji berry, the fig and the persimmon leaf with hot water and mixing the three extracts at a ratio of 1:1:1 and 2:1:2, respectively; and the group mixing the goji berry, the fig and the persimmon leaf of 17.5, 10.8 and 71.7 parts by weight, respectively, and then extracting and spray drying the mixture, it was confirmed that the melanin production was reduced.

TEST EXAMPLE 5

Measurement of Keratinocyte-derived MMP-1 Gene Expression 5-1. Cell Culture

Human keratinocyte cell line, HaCaT cells were cultured in a 100 mm cell culture dish with DMEM medium containing penicillin (100 IU/ml), streptomycin (100 μg/ml) and 10% FBS to the density of 70% to 80%.

5-2. Measurement of MMP-1 Gene Expression

In order to examine the degree of MMP-1 expression at the transcription level, each sample was treated to the cells for a predetermined time, UVB was irradiated thereto. Then total RNA was extracted by using Trizol reagent. cDNA was manufactured from the extracted total RNA by using a First strand cDNA synthesis kit (Thermo scientific), and the same amount of cDNA was amplified by PCR. At this time, the sense and antisense primer sequences of the used target protein were manufactured by referring the existing documents, GAPDH was used as a control gene. PCR amplification was performed by using a Hipi PCR kit (Elpis biotech) 20 μl containing dNTP 250 μM, Tris-HCL (pH 8.3) 10 mM, KCl 50 mM, $NgCl_2$ 1.5 mM, with each test group cDNA, MMP-1 primers and control GAPDH primers. PCR was performed 30 cycles at the condition of denaturing at 95° C. for 45 sec, annealing at 60° C. for 45 sec and extension at 72° C. for 1 min. The DNA amplified by PCR was subjected to electrophoresis on a 1.5 agarose gel. The intensity of the fractionated DNA band was measured, and the results were shown in FIG. 5.

MMP-1 forward 5'-ATT CTA CTG ATA TCG GGG CTT TGA-3', MMP-1 reverse 5'-ATG TCC TTG GGG TAT CCG TGT AG-3'

Glyceraldehyde 3-phosphate dehydrogenase (GAPDH) forward 5'-CCA GCC GAG CCA CAT CGC TC-3', GAPDH reverse 5'-TGA CCT TGG CCA GGG GTG CT-3'

Figure 5:
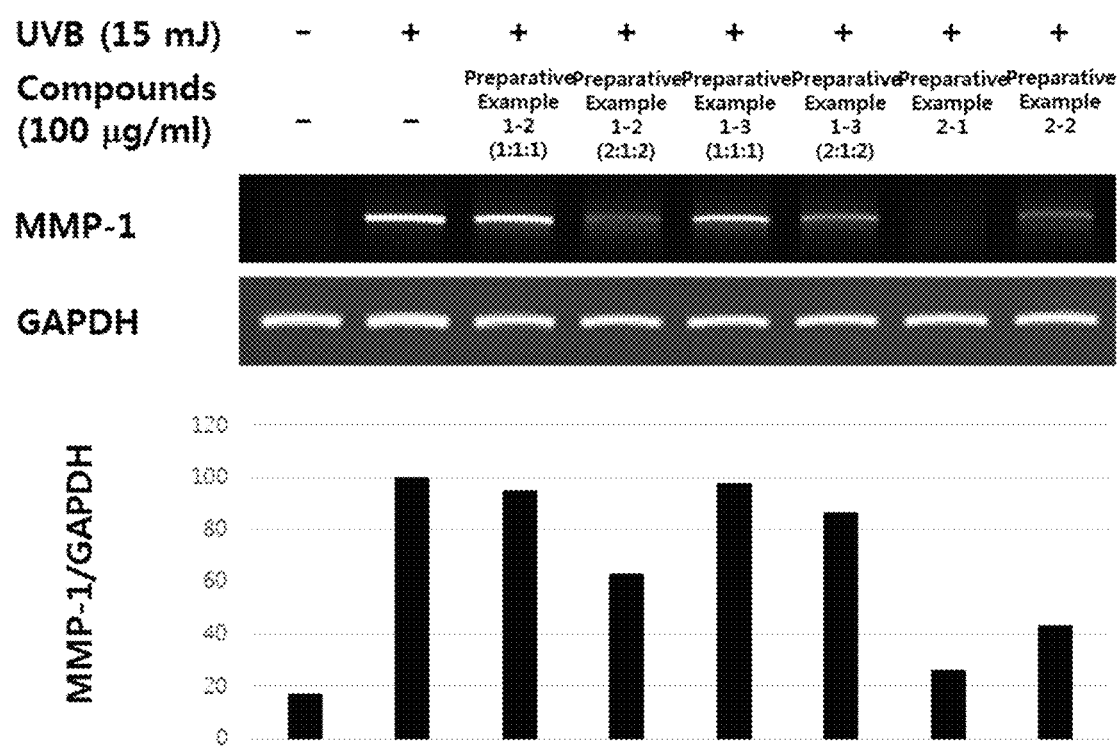
FIG. 5 is the result of electrophoresis showing the effect of the natural complex extract on the inhibition of keratinocyte-derived MMP-1 gene expression.

As shown in FIG. 5, from the results of measuring the MMP-1 gene expression at the group extracting each of the goji berry, the fig and Korean mint with hot water and then mixing the three extracts at a ratio of 1:1:1 and 2:1:2; and the group mixing the goji berry, the fig and Korean mint of 14.93, 9.29 and 75.78 parts by weight, respectively, and then extracting and spray drying the mixture, it was confirmed that the gene expression was reduced. From the results of measuring the MMP-1 gene expression at the group extracting each of the goji berry, the fig and the persimmon leaf with hot water and then mixing the three extracts at a ratio of 1:1:1 and 2:1:2; and the group mixing the goji berry, the fig and the persimmon leaf of 17.5, 10.8 and 71.7 parts by weight, respectively, and then extracting and spray drying the mixture, it was confirmed that the gene expression was reduced.

As can be seen form the result of Test Examples, the composition comprising a natural complex extract according to the present invention exhibits effects on antioxidation, immune enhancement, whitening, collagenase inhibition and anti-wrinkle, and the effects result from the synergistic action among the extract of goji berry, fig and Korean mint or the extract of goji berry, fig and persimmon leaf.

Although exemplary embodiments of the present disclosure have been described for illustrative purposes, those skilled in the art will appreciate that various modifications, additions and substitutions are possible, without departing from the scope and spirit of the disclosure. Therefore, exemplary embodiments of the present disclosure have not been described for limiting purposes. Accordingly, the scope of the disclosure is not to be limited by the above embodiments but by the claims and the equivalents thereof.

What is claimed is:

1. A composition comprising an extract of goji berry, fig and Korean mint, wherein the extract is effective for immune enhancement, for skin whitening, or a combination thereof, and wherein the extract is prepared by extracting a mixture of 5-20 parts by weight of goji berry, 5-20 parts by weight of fig, and 60-90 parts by weight of Korean mint with hot water.

2. The composition according to claim 1, wherein the extract is contained in an amount of 0.01-100 parts by weight based on 100 parts by weight of the composition.

3. A composition comprising an extract of goji berry, fig and persimmon leaf, wherein the extract is effective for skin whitening, wherein the extract is prepared by extracting a mixture of 5-20 parts by weight of goji berry, 5-20 parts by weight of fig, and 60-90parts by weight persimmon leaf with hot water.

4. The composition according to claim 3, wherein the extract is contained in an amount of 0.01-100 parts by weight based on 100 parts by weight of the composition.

\* \* \* \* \*